(12) United States Patent
McCleary et al.

(10) Patent No.: US 8,518,050 B2
(45) Date of Patent: Aug. 27, 2013

(54) MODULAR TAPER ASSEMBLY DEVICE

(75) Inventors: Larry G. McCleary, Warsaw, IN (US);
Jonathan E. Carr, Warsaw, IN (US);
Joel C. Rhoades, Pierceton, IN (US);
David W. Daniels, Warsaw, IN (US)

(73) Assignee: Depuy Synthes Products, LLC, Raynham, MA (US)

( * ) Notice: Subject to any disclaimer, the term of this patent is extended or adjusted under 35 U.S.C. 154(b) by 1437 days.

(21) Appl. No.: 11/930,811

(22) Filed: Oct. 31, 2007

(65) Prior Publication Data
US 2009/0112218 A1 Apr. 30, 2009

(51) Int. Cl.
*A61F 2/00* (2006.01)
*A61F 2/42* (2006.01)

(52) U.S. Cl.
USPC .......................................... 606/99; 623/22.12

(58) Field of Classification Search
USPC .................. 606/254, 99, 151, 29; 623/22.12; 269/32, 3, 6
See application file for complete search history.

(56) References Cited

U.S. PATENT DOCUMENTS

| | | | |
|---|---|---|---|
| 1,383,304 A | 7/1921 | Hughes | |
| 1,423,649 A | 7/1922 | Daniel | |
| 1,534,692 A | 4/1925 | Davis | |
| 2,631,584 A | 7/1948 | Purificato | |
| 2,661,033 A | 12/1953 | Daniel | |
| 2,711,196 A | 6/1955 | Daniel | |
| 2,834,382 A | 5/1958 | Daniel | |
| 2,856,637 A | 10/1958 | Daniel | |
| 2,864,282 A | 12/1958 | Daniel | |
| 2,877,936 A | 3/1959 | Michel | |
| 2,895,154 A | 7/1959 | Belcher | |
| 2,902,596 A | 9/1959 | Rockwell | |
| 2,914,224 A | 11/1959 | Michel | |
| 2,944,373 A | 7/1960 | Mentley | |
| 2,955,905 A | 10/1960 | Davies | |
| 2,957,610 A | 10/1960 | Michel | |
| 2,974,699 A | 3/1961 | Boles | |

(Continued)

FOREIGN PATENT DOCUMENTS

| | | |
|---|---|---|
| EP | 1080701 A2 | 3/2001 |
| EP | 1080701 A3 | 7/2001 |

(Continued)

OTHER PUBLICATIONS

European Search Report Dated Feb. 22, 2010 for Corresponding European Patent Application No. 08167776.7, 5 Pages.

(Continued)

*Primary Examiner* — Heidi M Eide (57) ABSTRACT

An assembly tool for assembly of a first component of a prosthesis to a second component of the prosthesis. The tool includes a housing defining a housing longitudinal axis thereof. An internal component is also provided and is connected to the second component and includes an actuating device and an actuator rod defining a second longitudinal axis that is coexistent with the housing longitudinal axis. The internal component is adapted to provide relative motion of the internal component with respect to the housing when the actuating device is moved relative to the housing in at least a direction transverse to the housing longitudinal axis and the actuator rod of the internal component is moved relative to the housing in a direction parallel to the housing longitudinal axis.

6 Claims, 6 Drawing Sheets

(56) References Cited

U.S. PATENT DOCUMENTS

| | | |
|---|---|---|
| 2,975,944 A | 3/1961 | Michel |
| 2,977,726 A | 4/1961 | Daniel |
| 2,981,035 A | 4/1961 | Mentley |
| 2,994,461 A | 8/1961 | Michel |
| 2,994,988 A | 8/1961 | Mentley |
| 3,048,307 A | 8/1962 | Michel |
| 3,059,278 A | 10/1962 | Daniel |
| 3,071,862 A | 1/1963 | Daniel |
| 3,077,877 A | 2/1963 | Daniel |
| 3,092,934 A | 6/1963 | Daniel |
| 3,092,935 A | 6/1963 | Daniel |
| 3,101,875 A | 8/1963 | Michel |
| 3,135,136 A | 6/1964 | Mentley |
| 3,180,532 A | 4/1965 | Michel |
| 3,220,311 A | 11/1965 | Anthony |
| 3,250,745 A | 5/1966 | Davis |
| 3,293,987 A | 12/1966 | Daniel |
| 3,295,987 A | 1/1967 | Hoshino |
| 3,300,833 A | 1/1967 | Daniel |
| 3,301,134 A | 1/1967 | Daniel |
| 3,319,526 A | 5/1967 | Daniel |
| 3,331,115 A | 7/1967 | Daniel |
| 3,335,639 A | 8/1967 | Daniel |
| 3,424,783 A | 1/1969 | Harper |
| 3,443,478 A | 5/1969 | Daniel |
| 3,451,111 A | 6/1969 | Daniel |
| 3,479,387 A | 11/1969 | Daniels |
| 3,479,388 A | 11/1969 | Daniels |
| 3,483,175 A | 12/1969 | Harper |
| 3,494,752 A | 2/1970 | Daniel |
| 3,499,920 A | 3/1970 | Daniels |
| 3,541,868 A | 11/1970 | Hall |
| 3,580,027 A | 5/1971 | Daniel |
| 3,580,029 A | 5/1971 | Daniel |
| 3,604,235 A | 9/1971 | Motz |
| 3,629,981 A | 12/1971 | McCaffery |
| 3,631,703 A | 1/1972 | Bregi |
| 3,668,139 A | 6/1972 | Daniels |
| 3,673,887 A | 7/1972 | Daniel |
| 3,679,728 A | 7/1972 | Morgan |
| 3,679,729 A | 7/1972 | Daniels |
| 3,691,718 A | 9/1972 | Woodruff et al. |
| 3,700,957 A | 10/1972 | Daniels |
| 3,705,513 A | 12/1972 | Daniel |
| 3,754,586 A | 8/1973 | Daniels |
| 3,810,312 A | 5/1974 | Carson |
| 3,849,322 A | 11/1974 | Wendler |
| 3,869,394 A | 3/1975 | Daniels |
| 3,889,558 A | 6/1975 | Duncan |
| 3,912,727 A | 10/1975 | Daniels |
| 4,009,712 A | 3/1977 | Burstein |
| 4,035,988 A | 7/1977 | Daniels |
| D246,507 S | 11/1977 | Danielson |
| 4,150,909 A | 4/1979 | Hibarger |
| D257,533 S | 11/1980 | Bevilacqua |
| D258,957 S | 4/1981 | Bevilacqua |
| 4,305,394 A | 12/1981 | Bertuch, Jr. |
| D266,768 S | 11/1982 | Bevilacqua |
| D267,151 S | 12/1982 | Bruce |
| 4,398,074 A | 8/1983 | Danielson |
| D275,006 S | 8/1984 | Danielson |
| D282,246 S | 1/1986 | Thomas |
| D282,350 S | 1/1986 | Thomas |
| 4,601,289 A | 7/1986 | Chiarizzio |
| D285,073 S | 8/1986 | Danielson |
| D285,198 S | 8/1986 | Danielson |
| D286,198 S | 10/1986 | Bancroft |
| D286,285 S | 10/1986 | Danielson |
| D287,494 S | 12/1986 | Danielson |
| D289,155 S | 4/1987 | Brooks |
| D290,399 S | 6/1987 | Kitchens |
| 4,686,971 A | 8/1987 | Harris et al. |
| 4,710,946 A | 12/1987 | Hinch |
| 4,716,894 A | 1/1988 | Lazzeri |
| D303,114 S | 8/1989 | Danielson |
| D304,587 S | 11/1989 | Danielson |
| 4,891,545 A | 1/1990 | Capek |
| 4,917,530 A | 4/1990 | Engelhardt |
| 4,923,422 A | 5/1990 | Capek |
| 4,959,066 A | 9/1990 | Dunn |
| 4,969,911 A | 11/1990 | Greene |
| D313,233 S | 12/1990 | Andrews, Sr. |
| D315,343 S | 3/1991 | Andrews |
| 4,997,621 A | 3/1991 | Johansson |
| 5,002,581 A | 3/1991 | Paxson |
| 5,020,519 A | 6/1991 | Hayes |
| D318,051 S | 7/1991 | Danielson |
| D319,439 S | 8/1991 | Danielson |
| 5,049,150 A | 9/1991 | Cozad |
| D320,985 S | 10/1991 | Danielson |
| 5,060,505 A | 10/1991 | Tury |
| D323,657 S | 2/1992 | Danielson |
| 5,099,714 A | 3/1992 | Hutchison |
| 5,100,407 A | 3/1992 | Conrad |
| 5,133,588 A | 7/1992 | Hutchinson |
| 5,135,529 A | 8/1992 | Paxson |
| 5,162,626 A | 11/1992 | Hutchison |
| 5,171,055 A | 12/1992 | Hutchison |
| 5,184,017 A | 2/1993 | Tury |
| 5,197,989 A | 3/1993 | Hinckfuss |
| 5,201,882 A | 4/1993 | Paxson |
| 5,218,814 A | 6/1993 | Teal |
| D337,639 S | 7/1993 | Beckman |
| D338,473 S | 8/1993 | Patterson |
| 5,238,267 A | 8/1993 | Hutchison |
| 5,247,171 A | 9/1993 | Wlodarczyk |
| D340,461 S | 10/1993 | Patterson |
| 5,331,124 A | 7/1994 | Danielson |
| 5,342,363 A | 8/1994 | Richelsoph |
| 5,345,483 A | 9/1994 | Johansson |
| 5,352,231 A | 10/1994 | Brumfield |
| D352,521 S | 11/1994 | Sculler |
| D353,394 S | 12/1994 | Stefanski |
| 5,370,706 A | 12/1994 | Bolesky |
| D355,186 S | 2/1995 | Danielson |
| D355,187 S | 2/1995 | Danielson |
| 5,409,492 A | 4/1995 | Jones |
| 5,420,910 A | 5/1995 | Rudokas |
| D359,064 S | 6/1995 | Sculler |
| 5,422,478 A | 6/1995 | Wlodarczyk |
| 5,457,100 A | 10/1995 | Daniel |
| 5,459,294 A | 10/1995 | Danielson |
| D364,621 S | 11/1995 | Clarke |
| 5,476,466 A | 12/1995 | Barrette et al. |
| D365,824 S | 1/1996 | Danielson |
| 5,507,824 A | 4/1996 | Lennox |
| 5,507,830 A | 4/1996 | DeMane |
| 5,528,640 A | 6/1996 | Johansson |
| 5,555,551 A | 9/1996 | Rudokas |
| D376,527 S | 12/1996 | Apolinski |
| 5,600,892 A | 2/1997 | Peugh |
| 5,601,567 A | 2/1997 | Swajger |
| 5,607,431 A | 3/1997 | Dudasik |
| D379,578 S | 6/1997 | Daniels |
| 5,645,607 A | 7/1997 | Hickey |
| 5,658,349 A | 8/1997 | Brooks |
| 5,663,993 A | 9/1997 | Danielson |
| 5,669,812 A | 9/1997 | Schockemoehl |
| D387,962 S | 12/1997 | Apolinski |
| D387,963 S | 12/1997 | Clark |
| 5,715,672 A | 2/1998 | Schockemoehl |
| D392,534 S | 3/1998 | Degen |
| D392,866 S | 3/1998 | Degen |
| 5,728,128 A | 3/1998 | Crickenberger |
| 5,735,857 A | 4/1998 | Lane |
| 5,766,261 A | 6/1998 | Neal |
| 5,776,200 A | 7/1998 | Johnson |
| 5,792,143 A | 8/1998 | Samuelson |
| 5,804,886 A | 9/1998 | Danielson |
| 5,810,829 A | 9/1998 | Elliott |
| 5,810,830 A | 9/1998 | Noble |
| 5,849,015 A | 12/1998 | Haywood et al. |
| 5,850,162 A | 12/1998 | Danielsons |
| 5,858,020 A | 1/1999 | Johnson |

| Patent | Date | Name |
|---|---|---|
| 5,858,828 A | 1/1999 | Seliskar |
| 5,860,969 A | 1/1999 | White |
| 5,876,459 A | 3/1999 | Powell |
| 5,879,391 A | 3/1999 | Slamin |
| 5,902,340 A | 5/1999 | White et al. |
| 5,906,644 A | 5/1999 | Powell |
| 5,919,195 A | 7/1999 | Wilson |
| 5,923,422 A | 7/1999 | Keens |
| 5,935,172 A | 8/1999 | Ochoa |
| 5,950,121 A | 9/1999 | Kaminsky |
| 5,951,606 A | 9/1999 | Burke |
| 5,954,460 A | 9/1999 | Degen |
| 5,957,768 A | 9/1999 | Schockemoehl |
| 5,966,599 A | 10/1999 | Walker |
| 5,973,064 A | 10/1999 | Zhao |
| 5,976,147 A | 11/1999 | LaSalle |
| 5,976,188 A | 11/1999 | Dextradeur |
| 5,993,455 A | 11/1999 | Noble |
| 5,996,812 A | 12/1999 | Sokol, Jr. |
| 5,997,419 A | 12/1999 | Daniels |
| 6,045,556 A | 4/2000 | Cohen |
| 6,054,895 A | 4/2000 | Danielsons |
| 6,056,084 A | 5/2000 | Schockemoehl |
| 6,058,301 A | 5/2000 | Daniels |
| 6,059,528 A | 5/2000 | Danielson |
| 6,063,123 A | 5/2000 | Burrows et al. |
| 6,069,048 A | 5/2000 | Daniel |
| 6,071,311 A | 6/2000 | O'Neil |
| 6,077,783 A | 6/2000 | Allman |
| 6,080,162 A | 6/2000 | Dye |
| 6,096,625 A | 8/2000 | Daniel |
| 6,117,138 A | 9/2000 | Burrows |
| 6,121,147 A | 9/2000 | Daniel |
| 6,126,694 A | 10/2000 | Gray, Jr. |
| 6,165,177 A | 12/2000 | Wilson |
| 6,179,116 B1 | 1/2001 | Noniewicz |
| 6,179,877 B1 | 1/2001 | Burke |
| 6,181,925 B1 | 1/2001 | Kaminsky |
| 6,185,416 B1 | 2/2001 | Rudokas |
| 6,193,759 B1 | 2/2001 | Ro |
| 6,197,065 B1 | 3/2001 | Martin |
| 6,201,253 B1 | 3/2001 | Allman |
| 6,206,884 B1 | 3/2001 | Masini |
| 6,219,538 B1 | 4/2001 | Kaminsky |
| 6,224,605 B1 | 5/2001 | Anderson |
| 6,232,721 B1 | 5/2001 | Danielsons |
| 6,235,590 B1 | 5/2001 | Daniel |
| 6,238,435 B1 | 5/2001 | Meulink |
| D443,882 S | 6/2001 | Daniels |
| 6,241,847 B1 | 6/2001 | Allman |
| 6,242,978 B1 | 6/2001 | Danielsons |
| 6,258,095 B1 | 7/2001 | Lombardo |
| 6,258,097 B1 | 7/2001 | Cook |
| 6,260,279 B1 | 7/2001 | Apolinski |
| 6,263,998 B1 | 7/2001 | Schockemoehl |
| 6,281,935 B1 | 8/2001 | Twitchell |
| 6,285,871 B1 | 9/2001 | Daniels |
| 6,310,410 B1 | 10/2001 | Lin |
| D450,304 S | 11/2001 | Daniels |
| 6,316,817 B1 | 11/2001 | Seliskar |
| 6,319,286 B1 | 11/2001 | Fernandez et al. |
| 6,330,845 B1 | 12/2001 | Meulink |
| 6,332,886 B1 | 12/2001 | Green |
| 6,335,766 B1 | 1/2002 | Twitchell |
| 6,354,908 B2 | 3/2002 | Allman |
| 6,355,068 B1 | 3/2002 | Doubler |
| 6,355,532 B1 | 3/2002 | Seliskar |
| 6,361,563 B2 | 3/2002 | Terrill Grisoni |
| 6,366,422 B1 | 4/2002 | Daniel |
| 6,372,520 B1 | 4/2002 | Hsia |
| D457,176 S | 5/2002 | Daniels |
| 6,382,276 B1 | 5/2002 | Daniels |
| D458,947 S | 6/2002 | Svetlik |
| 6,400,415 B1 | 6/2002 | Danielsons |
| 6,406,217 B1 | 6/2002 | Daniel |
| 6,419,147 B1 | 7/2002 | Daniel |
| 6,422,562 B1 | 7/2002 | Daniel |
| 6,422,816 B1 | 7/2002 | Danielson |
| 6,428,578 B2 | 8/2002 | White |
| 6,432,110 B1 | 8/2002 | Richelsoph |
| D467,485 S | 12/2002 | Daniels |
| 6,488,713 B1 | 12/2002 | Hershberger |
| D468,180 S | 1/2003 | Bruno |
| 6,506,684 B1 | 1/2003 | Daniel |
| 6,508,841 B2 | 1/2003 | Martin et al. |
| D469,671 S | 2/2003 | Prell |
| 6,517,581 B2 | 2/2003 | Blamey |
| 6,565,029 B2 | 5/2003 | Zweighaft |
| 6,568,618 B1 | 5/2003 | Vanderheyden |
| 6,589,284 B1 | 7/2003 | Silberer |
| 6,600,516 B1 | 7/2003 | Danielsons |
| 6,609,900 B2 | 8/2003 | Lucke |
| 6,682,568 B2 | 1/2004 | Despres, III et al. |
| 6,692,530 B2 | 2/2004 | Doubler et al. |
| 6,700,359 B2 | 3/2004 | Daniels |
| 6,702,854 B1 | 3/2004 | Cheal |
| 6,706,072 B2 | 3/2004 | Dwyer |
| 6,706,621 B2 | 3/2004 | Cox |
| 6,723,129 B2 | 4/2004 | Dwyer |
| 6,743,235 B2 | 6/2004 | Subba Rao |
| 6,744,243 B2 | 6/2004 | Daniels et al. |
| 6,751,266 B1 | 6/2004 | Danielsons |
| 6,793,208 B1 * | 9/2004 | Riddle et al. ................ 269/3 |
| D497,499 S | 10/2004 | Daniel |
| 6,811,376 B2 | 11/2004 | Arel |
| 6,812,792 B2 | 11/2004 | Mattsson |
| 6,856,029 B1 | 2/2005 | Daniel |
| 6,870,160 B1 | 3/2005 | Daniel |
| 6,883,217 B2 | 4/2005 | Barrette |
| D505,611 S | 5/2005 | Daniel |
| 6,905,515 B1 | 6/2005 | Gilbertson |
| 6,911,048 B2 | 6/2005 | Fernandez et al. |
| 6,949,101 B2 | 9/2005 | McCleary |
| 6,990,691 B2 | 1/2006 | Klotz |
| 7,022,141 B2 | 4/2006 | Dwyer |
| 7,582,092 B2 | 9/2009 | Jones et al. |
| 2001/0001121 A1 | 5/2001 | Lombardo |
| 2001/0007957 A1 | 7/2001 | Martin |
| 2001/0021622 A1 | 9/2001 | Allman |
| 2002/0043296 A1 | 4/2002 | Daniels |
| 2002/0058999 A1 | 5/2002 | Dwyer |
| 2002/0059000 A1 | 5/2002 | Dwyer |
| 2002/0127115 A1 | 9/2002 | Lucke |
| 2002/0195512 A1 | 12/2002 | Zweighft |
| 2003/0001551 A1 | 1/2003 | Daniels |
| 2003/0048003 A1 | 3/2003 | Daniels |
| 2003/0050645 A1 | 3/2003 | Parker |
| 2003/0071329 A1 | 4/2003 | Cox |
| 2003/0095368 A1 | 5/2003 | Daniels |
| 2003/0180146 A1 | 9/2003 | Arel |
| 2003/0187449 A1 | 10/2003 | McCleary |
| 2003/0204269 A1 | 10/2003 | Gerbec et al. |
| 2003/0228033 A1 | 12/2003 | Daniel |
| 2004/0017085 A1 | 1/2004 | Daniels |
| 2004/0054373 A1 | 3/2004 | Serra et al. |
| 2004/0058997 A1 | 3/2004 | Daniel |
| 2004/0064186 A1 | 4/2004 | McCleary et al. |
| 2004/0066217 A1 | 4/2004 | Daniels |
| 2004/0073315 A1 | 4/2004 | Justin et al. |
| 2004/0122437 A1 | 6/2004 | Dwyer |
| 2004/0122439 A1 | 6/2004 | Dwyer |
| 2004/0122440 A1 | 6/2004 | Daniels |
| 2004/0122525 A1 | 6/2004 | Daniels |
| 2004/0130394 A1 | 7/2004 | Mattsson |
| 2004/0135233 A1 | 7/2004 | Cox |
| 2004/0172139 A1 | 9/2004 | Dwyer |
| 2004/0210471 A1 | 10/2004 | Luby |
| 2004/0267266 A1 | 12/2004 | Daniels |
| 2004/0267267 A1 | 12/2004 | Daniels |
| 2004/0267373 A1 | 12/2004 | Dwyer |
| 2005/0004679 A1 | 1/2005 | Sederholm et al. |
| 2005/0010992 A1 | 1/2005 | Klotz |
| 2005/0015049 A1 | 1/2005 | Rioux |
| 2005/0033444 A1 | 2/2005 | Jones |
| 2005/0047239 A1 | 3/2005 | Takahashi |
| 2005/0078289 A1 | 4/2005 | Daniel |
| 2005/0081910 A1 | 4/2005 | Danielson |
| 2005/0115391 A1 | 6/2005 | Baker |

| | | | |
|---|---|---|---|
| 2005/0154331 A1 | 7/2005 | Christie | |
| 2005/0188878 A1 | 9/2005 | Baker | |
| 2005/0209597 A1 | 9/2005 | Long et al. | |
| 2005/0234559 A1 | 10/2005 | Fernandez et al. | |
| 2005/0261702 A1* | 11/2005 | Oribe et al. | 606/103 |
| 2005/0267937 A1 | 12/2005 | Daniels | |
| 2005/0288676 A1 | 12/2005 | Schnieders | |
| 2006/0058810 A1 | 3/2006 | Wozencroft et al. | |
| 2006/0217737 A1 | 9/2006 | Iversen | |

FOREIGN PATENT DOCUMENTS

| | | |
|---|---|---|
| EP | 0728449 B1 | 7/2002 |
| EP | 1191906 B1 | 6/2005 |
| EP | 1080701 B1 | 8/2006 |
| FR | 2626212 A1 | 7/2009 |
| WO | WO 9615739 A1 | 5/1996 |
| WO | WO 01/67997 A1 | 9/2001 |

OTHER PUBLICATIONS

Gray, John R., "Clinically-Oriented Geometry of the Femur", A thesis submitted to the School of Physical & Health Education in partial fulfillment of requirements for the degree of Master of Science, Queen's University, Kingston, Ontario, Canada, Aug. 1995, 73 pages.

Zimmer, "Metasul LDH Large Diameter Head," Surgical Technique Enhancing Stability and Increasing Range of Motion, available at least as early as Sep. 28, 2006 (19 pages).

* cited by examiner

MODULAR TAPER ASSEMBLY DEVICE

TECHNICAL FIELD OF THE INVENTION

The present invention relates generally to the field of orthopaedics, and more particularly, to an implant for use in arthroplasty.

BACKGROUND OF THE INVENTION

Patients who suffer from the pain and immobility caused by osteoarthritis and rheumatoid arthritis have an option of joint replacement surgery. Joint replacement surgery is quite common and enables many individuals to function properly when it would not be otherwise possible to do so. Artificial joints are usually comprised of metal, ceramic and/or plastic components that are fixed to existing bone.

Such joint replacement surgery is otherwise known as joint arthroplasty. Joint arthroplasty is a well-known surgical procedure by which a diseased and/or damaged joint is replaced with a prosthetic joint. In a typical total joint arthroplasty, the ends or distal portions of the bones adjacent to the joint are resected or a portion of the distal part of the bone is removed and the artificial joint is secured thereto.

There are known to exist many designs and methods for manufacturing implantable articles, such as bone prostheses. Such bone prostheses include components of artificial joints such as elbows, hips, knees and shoulders.

During performance of a joint replacement procedure, it is generally necessary to provide the surgeon with a certain degree of flexibility in the selection of a prosthesis. In particular, the anatomy of the bone into which the prosthesis is to be implanted may vary somewhat from patient to patient. Such variations may be due to, for example, the patient's age, size and gender. For example, in the case of a femoral prosthesis, the patient's femur may be relatively long or relatively short thereby requiring use of a femoral prosthesis, which includes a stem that is relatively long or short, respectively. Moreover, in certain cases, such as when use of a relatively long stem length is required, the stem must also be bowed in order to conform to the anatomy of the patient's femoral canal.

Such a need for prostheses of varying shapes and sizes thus creates a number of problems in regard to the use of a one-piece prosthesis. For example, a hospital or surgery center must maintain a relatively large inventory of prostheses in order to have the requisite mix of prostheses needed for certain situations, such as trauma situations and revision surgery. Moreover, since the bow of the stem must conform to the bow of the intramedullary canal of the patient's femur, rotational positioning of the upper portion of the prosthesis is limited thereby rendering precise location of the upper portion and hence the head of the prosthesis very difficult.

In addition, since corresponding bones of the left and right side of a patient's anatomy (e.g. left and right femur) may bow in opposite directions, it is necessary to provide (left) and (right) variations of the prosthesis in order to provide anteversion of the bone stem, thereby further increasing the inventory of prostheses which must be maintained.

As a result of these and other drawbacks, a number of modular prostheses have been designed. As its name implies, a modular prosthesis is constructed in modular form so that the individual elements or figures of the prosthesis can be selected to fit the needs of a given patient's anatomy. For example, modular prostheses have been designed which include a proximal neck component which can be assembled to any one of numerous distal stem components in order to create an assembly which fits the needs of a given patient's anatomy. Such a design allows the distal stem component to be selected and thereafter implanted in the patient's bone in a position that conforms to the patient's anatomy while also allowing for a limited degree of independent positioning of the proximal neck component relative to the patient's pelvis.

One issue that arises as a result of the use of a modular prosthesis is the locking of the components relative to one another. In particular, firm reproducible locking of the proximal neck component to the distal stem component is critical to prevent separation of the two components subsequent to implantation thereof into the patient. The need for the firm locking is particularly necessary if the design does not provide for positive locking with weight bearing. As such, a number of locking mechanisms have heretofore been designed to lock the components of a modular prosthesis to one another. For example, a number of modular prostheses have heretofore been designed to include a distal stem component, which has an upwardly extending post, which is received into a bore defined distal neck component. A relatively long fastener such as a screw or bolt is utilized to secure the post with the bore. Other methods of securing modular components include the impacting of one component onto the other. This method has highly variable results Current designs of modular stems include designs in which the modular connection utilizes a tapered fit between the two components. For example, the proximal body may include an internal taper, which mates with an external taper on the distal stem. Such a taper connection may be used in conjunction with additional securing means, for example, a threaded connection or may be used alone. It is important that the tapered connection be secure. For example, the proper amount of force must be applied to the tapered connection to properly secure the tapered connection so that the connection can withstand the forces associated with the operation of the stem.

Current attempts to provide a device to adjoin components of a modular joint prosthesis are fraught with several problems. For example, the device may not provide sufficient mechanical advantage to securely lock the components. Further, the ergonomics available to lock the components may not be optimal. Additionally, a device relying solely on the displacement for a taper connection may not provide sufficient force as there may not be an accurate correspondence of displacement to the clamping force. Also, utilizing a displacement method may make it possible to overtighten and damage the components. Further, prior art solutions may be difficult to manufacture or expensive to make.

Once a modular prosthesis, for example, a modular hip stem prosthesis, has its relative components positioned properly, the components must be firmly secured to each other. It is possible when the components are secured together that relative motion between the components may occur causing their relative position in particular their angular orientation to be disturbed. In other words, when the first and second components of the modular hip stem are drawn together, one component may rotate about the other one causing their version or orientation to be compromised. Further, whatever device is used to angularly position the components of the modular prosthesis into the proper orientation may need to be removed and an assembly device positioned on the prosthesis to secure the components to each other. Such removal of the alignment device and installation of the assembly device adds cost and complexity to the procedure, as well as, increasing the operating room time.

There is thus a need to provide for an assembly and disassembly tool capable of alleviating at least some of the aforementioned problems.

US Patent Application Publication No. 20040122439 entitled "ADJUSTABLE BIOMECHANICAL TEMPLATING & RESECTION INSTRUMENT AND ASSOCIATED METHOD", US Patent Application Publication No. 20040122437 entitled "ALIGNMENT DEVICE FOR MODULAR IMPLANTS AND METHOD", US Patent Application Publication No. 20040122440 entitled "INSTRUMENT AND ASSOCIATED METHOD OF TRAILING FOR MODULAR HIP STEMS", US Patent Application Publication No. 20040267266 published Jun. 25, 2003 entitled "MODULAR TAPERED REAMER FOR BONE PREPARATION AND ASSOCIATED METHOD", and US Patent Application Publication No. 20040267267 published Dec. 30, 2004 entitled "NON-LINEAR REAMER FOR BONE PREPARATION AND ASSOCIATED METHOD" are hereby incorporated in their entireties by reference.

Prior attempts to provide instruments to assemble modular prostheses have had problems due to the large and bulky nature of such instruments. These large and bulky instruments are difficult for the surgeon to use and provide problems in performing minimally invasive orthopedic implant surgery. Furthermore, prior art tools provide a tool designed for only one modular prosthesis. The tool may not be suitable for prostheses with other sizes and shapes. The present invention is directed to alleviate at least some of the problems with the prior art.

SUMMARY OF THE INVENTION

According to one embodiment of the present invention, an assembly tool for assembly of a first component of a prosthesis to a second component of the prosthesis for use in joint arthroplasty is provided. The tool includes a housing for contact with the first component. The housing defines a housing longitudinal axis thereof. An internal component is also provided and is connected to the second component. The internal component includes an actuating device and an actuator rod. The actuator rod defines an internal component longitudinal axis that is coexistent with the housing longitudinal axis. The housing and the internal component are adapted to provide for the assembly of the first component of the prosthesis to the second component of the prosthesis. The internal component is adapted to provide relative motion of the internal component with respect to the housing when the actuating device of the internal component is moved relative to the housing in at least a direction transverse to the internal component longitudinal axis and the actuator rod of the internal component is moved relative to the housing in a direction parallel to the internal component longitudinal axis for assembly of the first component of the prosthesis to the second component. The relative motion of the internal component with respect to the housing is utilized to effect the relative motion of the first component with respect to the second component to urge the second component into engagement with the first component.

According to another embodiment of the present invention, a kit for use in joint arthroplasty is provided. The kit includes a first component of a prosthesis, a second component of the prosthesis, and an assembly tool for assembling the first component to the second component. The tool includes a housing for contact with the first component and an internal component connected to the second component. The internal component includes an actuating device and an actuator rod. The actuating device having at least one scissor arm. The housing and the internal component are adapted to provide for the assembly of the first component of the prosthesis to the second component of the prosthesis. The internal component is adapted to provide relative motion of the internal component with respect to the housing when the at least one scissor arm is moved relative to the housing, the relative motion of the internal component with respect to the housing being utilized to effect the relative motion of the first component with respect to the second component to urge the second component into engagement with the first component.

According to yet another embodiment of the present invention, a method for providing joint arthroplasty is provided. The method includes providing a first component and a second component removably attachable to the first component. An instrument having a housing operably associated with the first component is provided. The housing defines a longitudinal axis. The housing also includes an internal component operably associated with the second component. The internal component includes the actuating device and an actuator rod. The internal component is operably associated with the housing for relative motion there between for assembly of the first component of the prosthesis to the second component. The first component is assembled to the second component and the internal component of the tool is connected to the second component. The actuating device of the internal component is moved relative to the housing, such that the movement is at least in a direction transverse to the longitudinal axis. The actuator rod of the internal component is moved relative to the housing, the movement being along the longitudinal axis, the movement securing the first component to the second component.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
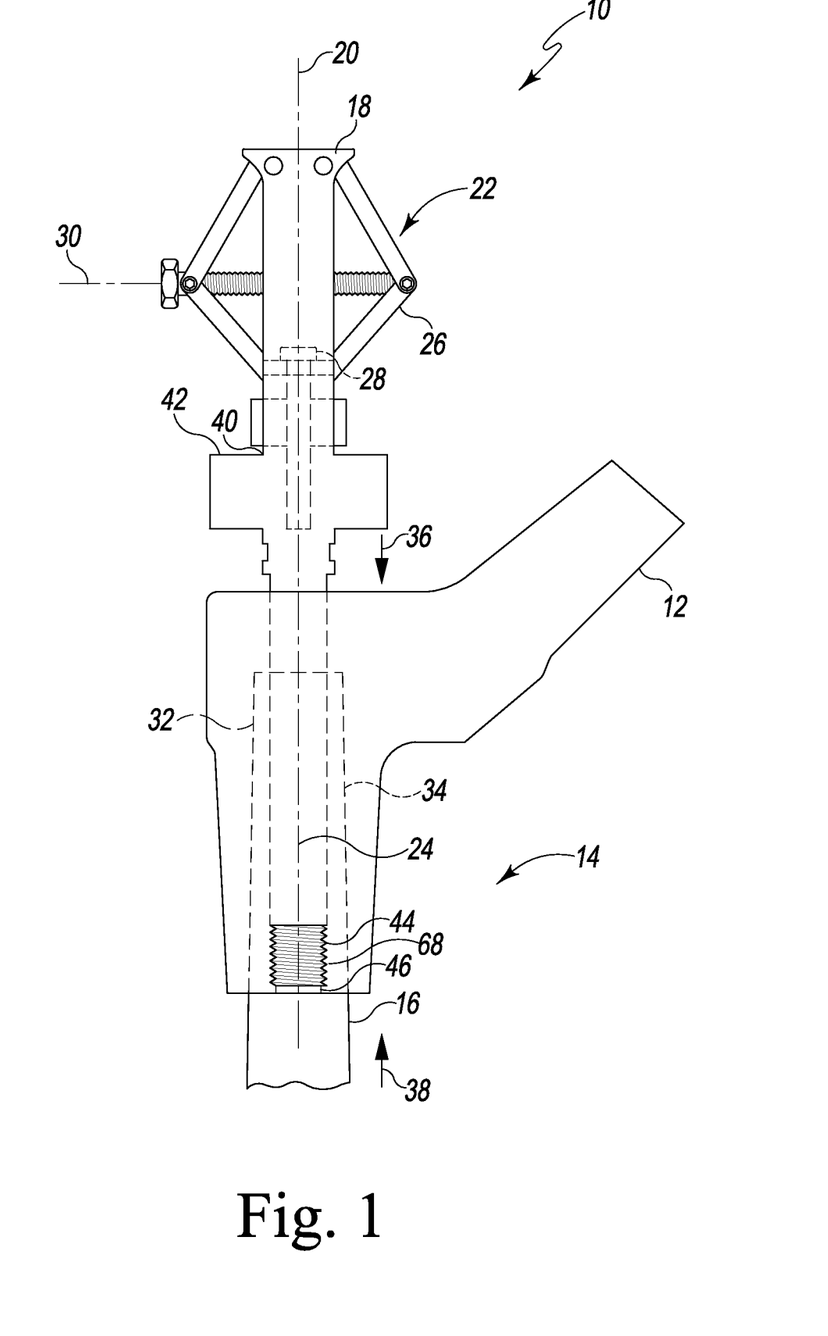
FIG. 1 is a plan view partially in cross-section of an embodiment of the present invention in the form of an assembly tool including a threaded connection in operation with a prosthesis.

According to the present invention and referring now to FIG. 1, assembly tool 10 according to the present invention is shown. The assembly tool 10 is used for assembly of a first component 12 of a prosthesis 14 to a second component 16 of the prosthesis 14 for use in joint arthroplasty. The tool 10 includes a housing 18 operably associated with the second component 16. The housing 18 defines a housing longitudinal axis 20 of the housing 18. The tool 10 also includes an internal component 22 operably associated with the second component 16. The internal component 22 defines an internal component longitudinal axis 24 of the internal component 22. The internal component 22 includes an actuating device 26 and an actuator rod 28 connected to the actuating device. The actuator rod defines a transverse axis 30 that is perpendicular to the internal component longitudinal axis 24. The internal component 22 is adapted to provide relative motion of the internal component 22 with respect to the housing 18 when the actuator rod 28 is rotated relative to the housing 18 about the transverse axis 30.

The assembly tool 10 is suited for use with the prosthesis 14 when, for example, the prosthesis 14 includes the first component 12 and the second component 16 which are engaged and disengaged by relative motions along an axis. For example, the assembly tool 10 is suitable when the prosthesis 14 includes components, which are connected by a tapered connection. For example, as shown in FIG. 1, the first component 12 includes an internal taper 32 that mates with an external taper 34 located on the second component 16.

As shown in FIG. 1, the first component 12 is engaged with the second component 16 when the first component 12 moves in the direction of arrow 36 and/or when the second component 16 moves in the direction of arrow 38. As shown in FIG. 1, the housing 18 is operably associated with the first component 12 while the internal component 22 is operably associated with the second component 16. To provide for the operable association of the components, it should be appreciated that the housing 18 includes a housing operating feature 40, which is operably associated with a first component operating feature 42 of the first component 12. Similarly, the internal component 22 includes an internal component operating feature 44, which cooperates with a second component operating feature 46 of the second component 16.

Figure 3:
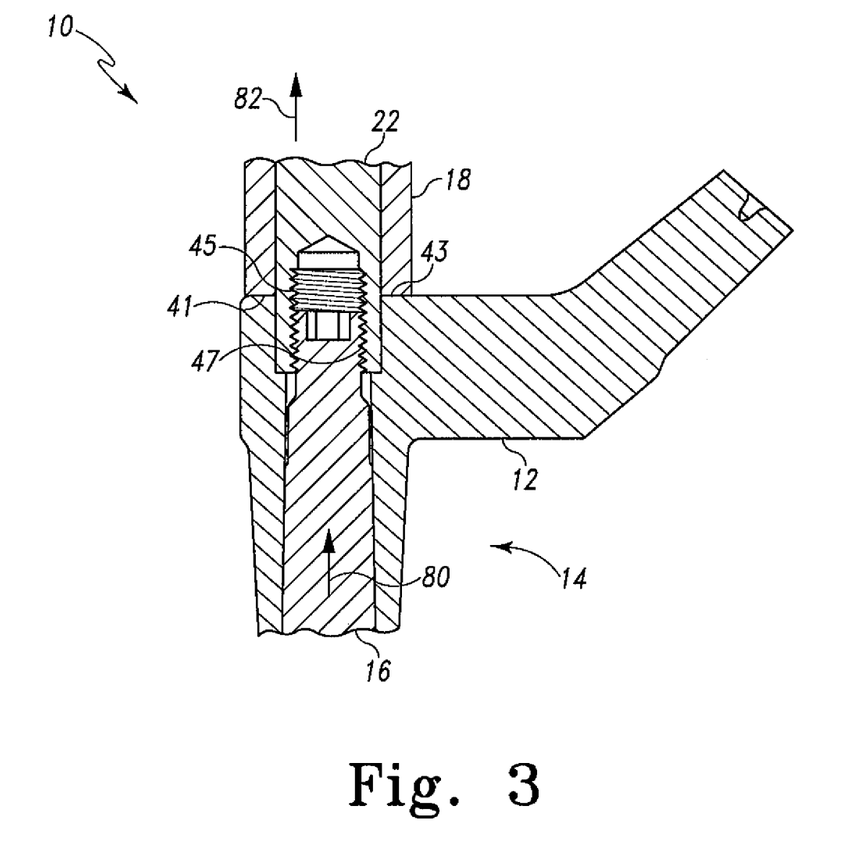
FIG. 3 is a cross section view of FIG. 2 along the line 3-3 in the direction of the arrows.

For simplicity, since the housing 18 and the first component 12 are merely required to prevent motion of the two components toward each other, the housing 18 and the first component 12 may be designed such that the housing operating feature 40 may be in the form of a bottom and/or surface 41 (FIG. 3). Similarly, the first component operating feature 42 may be in the form of a top surface 43 (FIG. 3) of the first component 12.

The internal component operating feature 44 and the second component operating feature 46 may be any features capable of urging the second component 16 upwardly in the direction of arrow 38. For example, for simplicity, the internal component operating feature 44 may be in the form of internal threads 47 (FIG. 3) formed on the second component operating feature 46, which may mate with external threads 45 (FIG. 3) formed on the second component 16.

The housing 18 and the internal component 22 may have any shape or configuration capable of providing relative motion along housing longitudinal axis 20 and internal component longitudinal axis 24. For example, and as shown in FIG. 1, the housing 18 may be in the form of a hollow component or tube. Similarly, the internal component 22 may be in the form of a rod or cylinder, which may slideably fit within the housing 18.

Figure 2:
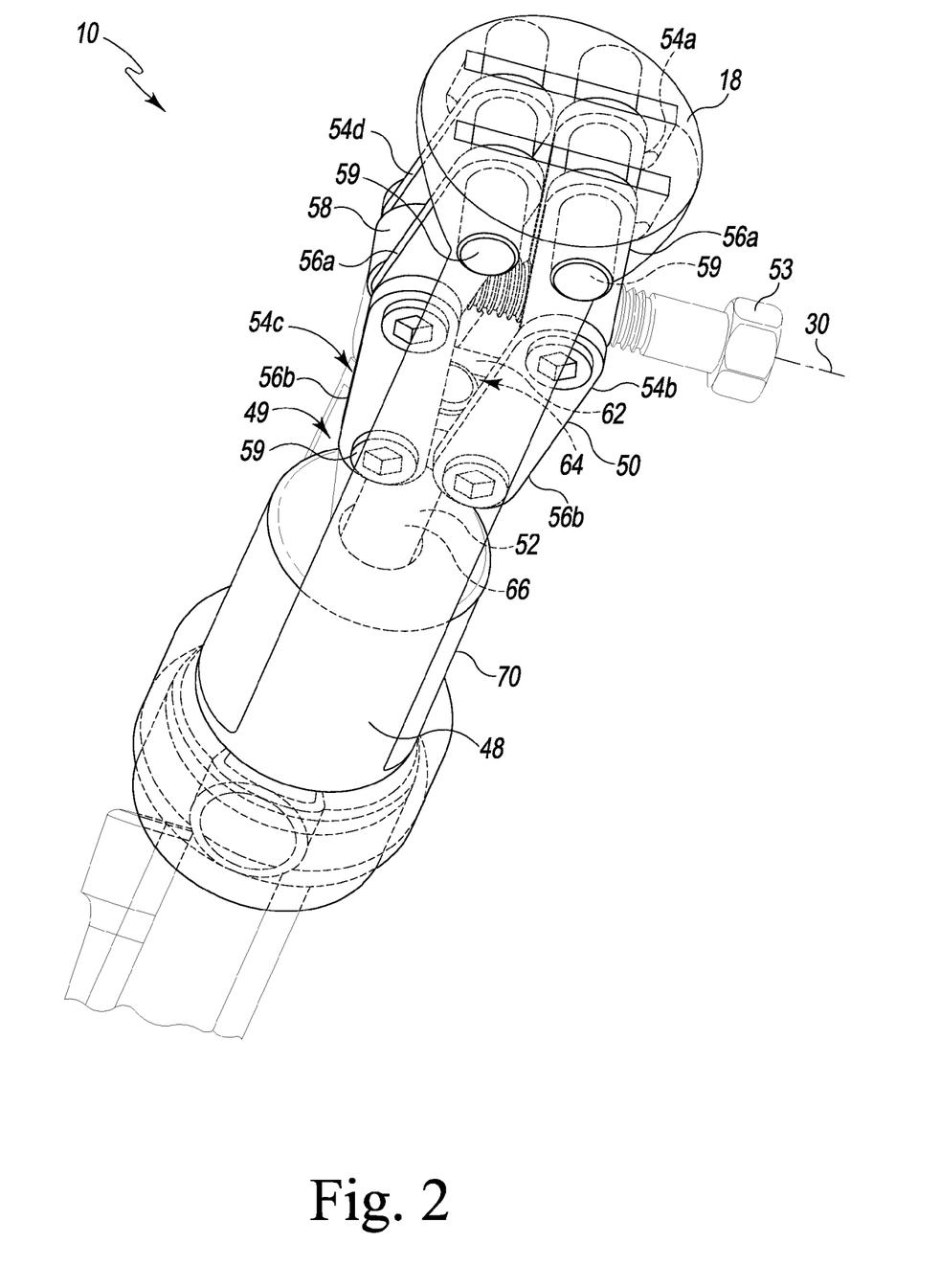
FIG. 2 is a perspective view of another embodiment of the present invention in the form of an assembly tool with a spiral cam and follower mechanism shown in engagement with a prosthesis.

Turning now to FIG. 2, in which a plan view of the instrument 10 is shown, the parts of the instrument 10 and their operation will be described in more detail. As shown, the housing 18 includes an outer housing 48 and the housing operating feature 40. The outer housing 48 also includes apertures 49 for coupling the outer housing 48 to the internal component 22.

The internal component 22 includes an actuating device 50 and an actuator rod 52. The actuating device 50 includes a screw 53 and four scissor members 54a, 54b, 54c, 54d. The scissor members 54a, 54b, 54c, 54d each include two legs 56a, 56b. The legs 56a, 56b are connected via a pin 58. One pair of scissor members 54a, 54b are also connected via the pin 58. The other pair of scissor members 54c, 54d are connected via the corresponding pin 58. The two pins 58 also connect the screw 53 to the scissor members 54a, 54b, 54c, 54d. Thus, when the screw 53 is rotated about the transverse axis 30, the four scissor members 54a, 54b, 54c, 54d expand and contract (like a car jack). The scissor members 54a, 54b, 54c, 54d are connected to the outer housing 48 via pins 59. The pins 59 extend through the apertures 49 in the outer housing 48.

The bottom portion of all four legs 56b are connected with a connecting member 62 that includes an aperture 64 for receiving a rod 66 that is a part of the actuator rod 52. The rod 66 extends longitudinally through the outer housing 48 of the housing 18. The bottom of the rod 66 includes the internal component operating feature 44, which in the illustrated embodiment is a threaded aperture 68. Surrounding and connected to the rod 68 is a cylinder 70. When a user turns the cylinder 70, the rod 66 also rotates. This can be used to connect the internal component operating feature 44 to the second component operating feature 46 (as shown in FIG. 1). The use of the scissor members 54a, 54b, 54c, 54d provide a greater mechanical advantage to the tool. By increasing the mechanical advantage through the use of the screw 53 and the scissor arms 54a, 54b, 54c, 54d, the amount of force that the user has to apply to the screw is greatly decreased from prior art designs.

Referring now to FIG. 3, the engagement of the assembly tool 10 with the prosthesis 14 is shown in greater detail. As shown in FIG. 3, the second component 16 includes a second component operating feature in the form of external threads 45. The external threads 45 are matingly fitted to, for example, internal threads 47 formed on internal component 22. The first component 12 includes an operating feature in the form of, for example, a top surface 43 which mates with bottom surface 41 of the housing 18 of the tool 10. In some embodiments, the threads may be Acme threads.

Since the housing 18 is in contact with the first component 12, when the first component is moved in the direction of arrow 80 relative to the first component 12, the internal component 22 is moved in the direction of arrow 82 relative to the housing 18. Thus, the relative motion of the internal component 22 with respect to the housing 18 in the direction of arrow 82 corresponds to the relative motion of the second component 16 with respect to the first component 12 in the direction of arrow 80.

Figure 4:
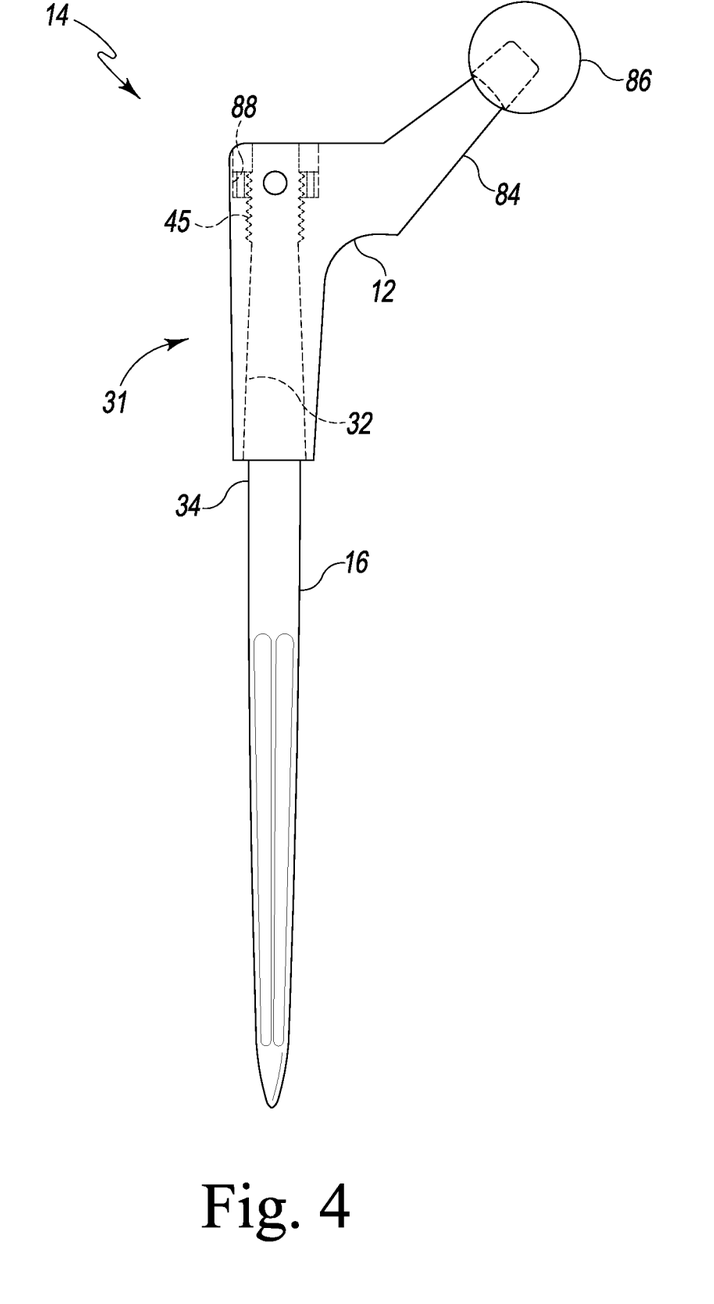
FIG. 4 is a plan view of a two pieced modular hip stem than may be assembled with the assembly tool of FIG. 2.

Referring now to FIG. 4, the prosthesis 14 is shown in greater detail. The prosthesis 14 as shown in FIG. 4 includes a taper connection 31. As shown in FIG. 4, the taper connection consists of the external taper 34 formed on the distal stem 16 that engages with internal taper 32 formed on the first component in the form of the proximal body 12.

It should be appreciated that the prosthesis for use with the assembly tool 10 of FIGS. 1 and 2, respectively, may include the first component 12 (in this case a proximal body) and the second component 16 (here a distal stem) which have an interference connection that is, for example, an interference connection of a cylindrical bore to a cylindrical stem, as well as, a splined non-uniform cross-section stem to a splined or non-uniform cross-section opening. It should further be appreciated that proximal body and distal stem of the prosthesis 14 for use with the assembly tool of the present invention may include a taper connection in which the distal stem has an internal taper and the proximal body has an external taper.

Again referring to FIG. 4, the prosthesis 14 as shown may include external threads 45 formed on the distal stem 16. The proximal body 12 may include a neck 84 to which a head 86 may matingly be fitted. As an additional precaution in assuring that the proximal body 12 remains secured to the distal stem 16, the prosthesis 14 may further include a nut 88 that threadably engages the external threads 45 of the distal stem 16.

Figure 5:
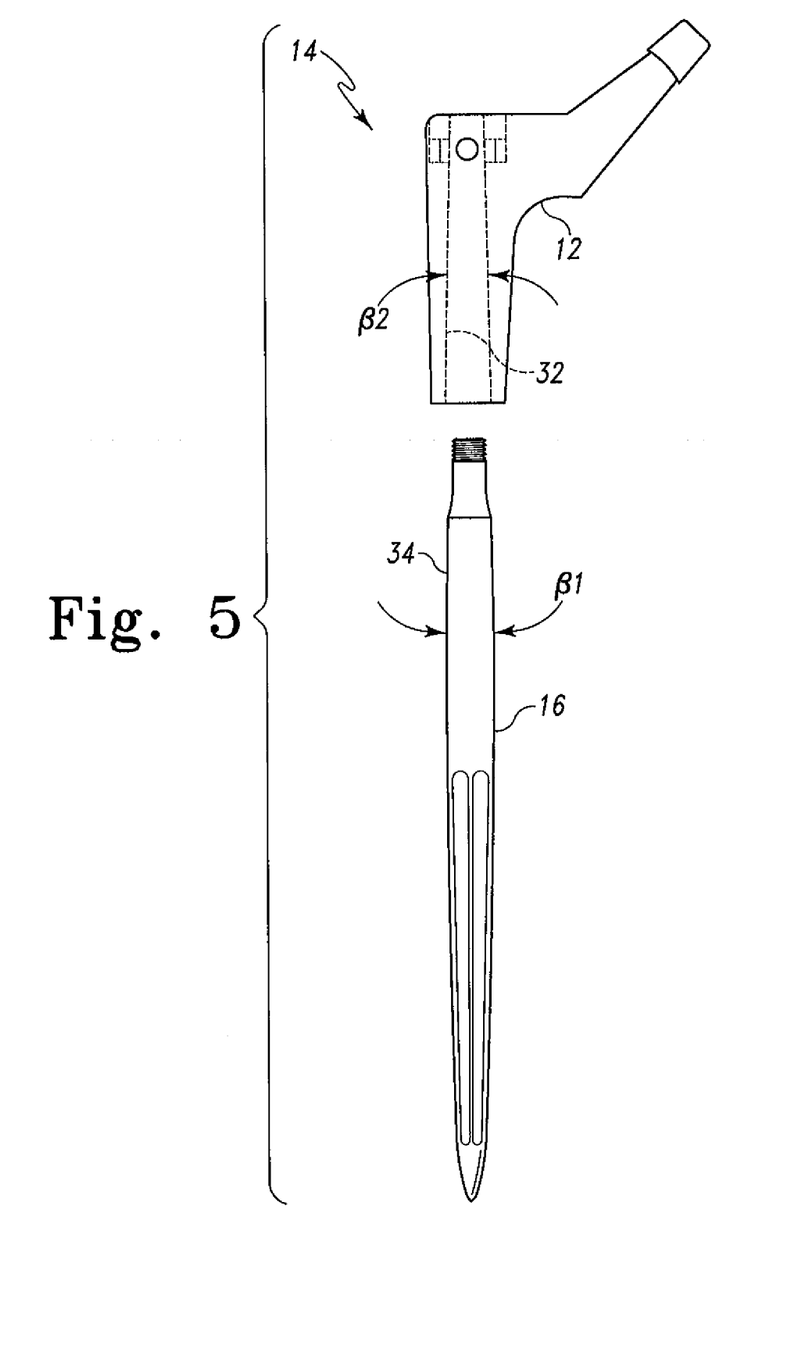
FIG. 5 is an exploded plan view of the modular hip stem of FIG. 4.

Referring now to FIG. 5, the prosthesis 14 is shown with the proximal body 12 disassembled from the distal stem 16. The external taper 34 of the distal stem 16 is defined by an included angle β1. In order that the proximal body 12 fits securely to the distal stem 16, the proximal body 12 includes the internal taper 32 defined by included angle β2. The angles β1 and β2 may be generally the same. Alternatively the taper angle may be divergent. The angles β1 and β2 should be chosen, such that the fit of the proximal body 12 to the distal stem 16 is secure.

In one embodiment, the instrument is made of stainless steel, however it is contemplated that other sterilizable metals may also be used.

Figure 6:
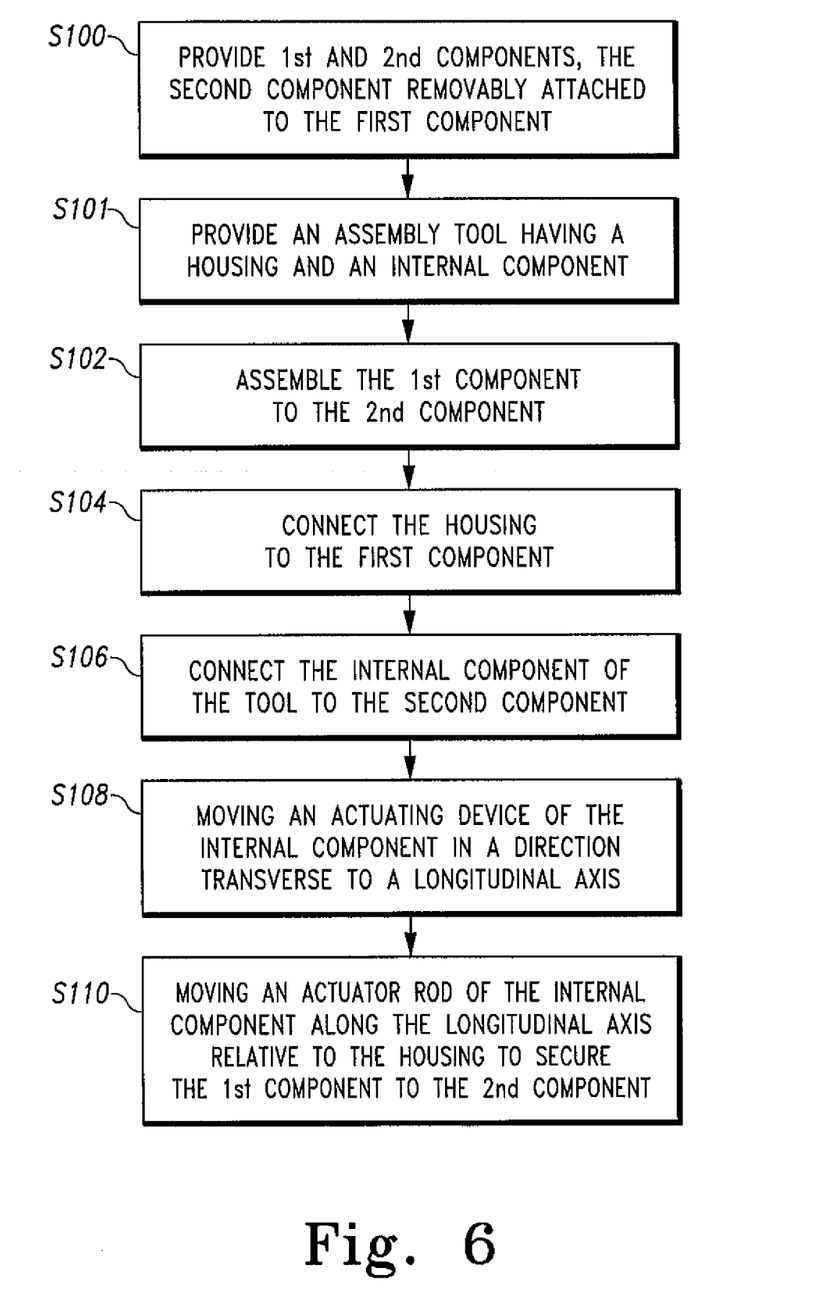
FIG. 6 is a flow chart of a method of using the assembly tool of the present invention according to another embodiment of the present invention.

Turning now to FIG. 6, a flow chart describing the operation of the assembly tool 10 according to one embodiment will be described. At step s100, a first component and a second component are provided. The second component is removably attachable to the first component. An assembly tool or instrument is also provided, the assembly tool including a housing and an internal component. The internal component includes an actuating device and an actuator rod (step s101). The first component is assembled to the second component at step s102. At step s104, the user connects the housing of the tool to the first component. The user also connects the internal component of the tool to the second component (step s106). At step s108, the user moves the actuating device of the internal component in a direction transverse to a longitudinal axis relative to the housing. The actuator rod of the internal component is then moved along the longitudinal axis relative to the housing to secure the first component to the second component (step 1110).

Although the present invention and its advantages have been described in detail, it should be understood that various changes, substitutions, and alterations can be made therein without departing from the spirit and scope of the present invention as defined by the appended claims.

We claim:

1. An assembly tool for assembly of a first component of a prosthesis to a second component of the prosthesis for use in joint arthroplasty, the tool comprising:

a housing for contact with the first component, the housing defining a housing longitudinal axis thereof; and an internal component connected to the second component, the internal component including an actuating device and an actuator rod, the actuator rod defining an internal component longitudinal axis that is coexistent with the housing longitudinal axis, the housing and the internal component being adapted to provide for the assembly of the first component of the prosthesis to the second component of the prosthesis, the internal component adapted to provide relative motion of the internal component with respect to the housing when the actuating device of the internal component is moved relative to the housing in at least a direction transverse to the internal component longitudinal axis and the actuator rod of the internal component is moved relative to the housing in a direction parallel to the internal component longitudinal axis for assembly of the first component of the prosthesis to the second component, the relative motion of the internal component with respect to the housing being utilized to effect the relative motion of the first component with respect to the second component to urge the second component into engagement with the first component; wherein the actuating device of the internal component includes a plurality of scissor arms, each of the scissor arms being connected at one end to the housing and at its opposite end to the actuator rod, each of the scissor arms consists of a pair of legs which are connected by means of a pin, a screw extends between the pins which interconnect the legs of each of the scissor arms such that, when the screw is rotated about its axis, it causes the distance between the pins to change measured in a direction which is transverse to the internal component longitudinal axis, and the distance between the ends of each of the scissor arms to change measured parallel to the internal component longitudinal axis.

2. The assembly tool of claim 1, wherein said plurality of scissor arms includes two pairs of scissor arms.

3. The assembly tool of claim 1, wherein the housing includes a housing operating feature for associating with an operating feature of the first component.

4. The assembly tool of claim 3, wherein the housing operating feature is an end surface for abutting the operating feature of the first component.

5. The assembly tool of claim 1, wherein the internal component includes an internal component operating feature for associating with an operating feature of the second component.

6. The assembly tool of claim 5, wherein the internal component operating feature is an internal thread for mating with an external thread of the operating feature of the second component.

* * * * *